United States Patent
Ziegler et al.

[11] Patent Number: 6,149,433
[45] Date of Patent: *Nov. 21, 2000

[54] ONE-PIECE IMPRESSION COPING FOR CUSTOMIZED IMPLANT RESTORATIVE SYSTEMS

[75] Inventors: Andrew Ziegler, Arlington; Thomas J. Cole, Cambridge, both of Mass.

[73] Assignee: Atlantis Components, Inc., Cambridge, Mass.

[*] Notice: This patent is subject to a terminal disclaimer.

[21] Appl. No.: 09/184,730

[22] Filed: Nov. 2, 1998

Related U.S. Application Data

[63] Continuation-in-part of application No. 08/851,836, May 5, 1997, Pat. No. 5,829,981.

[51] Int. Cl.⁷ ........................................ A61C 9/00
[52] U.S. Cl. ............................................... 433/214
[58] Field of Search .................................. 433/172, 173, 433/174, 175, 213, 214

[56] References Cited

U.S. PATENT DOCUMENTS

| | | | |
|---|---|---|---|
| D. 370,978 | 6/1996 | Broberg et al. | |
| 4,681,542 | 7/1987 | Baum | 433/172 |
| 4,758,161 | 7/1988 | Niznick | 433/173 |
| 4,955,811 | 9/1990 | Lazzara et al. | 433/173 |
| 4,988,297 | 1/1991 | Lazzara et al. | 433/173 |
| 5,052,929 | 10/1991 | Seal | 433/173 |
| 5,104,318 | 4/1992 | Piche et al. | 433/174 |
| 5,106,300 | 4/1992 | Voitik | 433/173 |
| 5,125,839 | 6/1992 | Ingber et al. | 433/169 |
| 5,125,841 | 6/1992 | Carlsson et al. | 433/213 |
| 5,193,999 | 3/1993 | Staubli | 433/72 |
| 5,213,502 | 5/1993 | Daftary | 433/172 |
| 5,297,963 | 3/1994 | Dafatry | 433/172 |
| 5,334,024 | 8/1994 | Niznick | 433/173 |
| 5,338,196 | 8/1994 | Beaty et al. | 433/172 |
| 5,362,235 | 11/1994 | Daftary | 433/172 |
| 5,362,237 | 11/1994 | Chalifoux | 433/220 |
| 5,417,568 | 5/1995 | Giglio | 433/173 |
| 5,419,702 | 5/1995 | Beaty et al. | 433/214 |
| 5,447,435 | 9/1995 | Brodbeck | 433/173 |
| 5,476,383 | 12/1995 | Beaty et al. | 433/214 |
| 5,492,471 | 2/1996 | Singer | 433/172 |
| 5,527,182 | 6/1996 | Willoughby | 433/172 |
| 5,571,015 | 11/1996 | Siegmund | 433/173 |
| 5,658,147 | 8/1997 | Phimmasone | 433/213 |
| 5,662,476 | 9/1997 | Ingber et al. | 433/213 |
| 5,674,073 | 10/1997 | Ingber et al. | 433/213 |
| 5,685,715 | 11/1997 | Beaty et al. | 433/173 |
| 5,688,123 | 11/1997 | Meiers et al. | 433/173 |
| 5,829,981 | 11/1998 | Ziegler | 433/214 |
| 5,938,443 | 8/1999 | Lazzara et al. | 433/214 |

FOREIGN PATENT DOCUMENTS

WO 96/34576  11/1996  WIPO .

OTHER PUBLICATIONS

Wheeler, *Dental Anatomy, Physiology and Occlusion* 3–23 (Fifth Edition, 1974).

*Primary Examiner*—Ralph A. Lewis
*Attorney, Agent, or Firm*—Testa, Hurwitz & Thibeault LLP

[57] ABSTRACT

An impression coping device for customized implant restorative systems comprises a head having an end for mating with a dental implant fixture. The mating end of the head has a plurality of axially extending, radially resilient fingers for a radial friction fit onto an implanted dental fixture.

10 Claims, 6 Drawing Sheets

ONE-PIECE IMPRESSION COPING FOR CUSTOMIZED IMPLANT RESTORATIVE SYSTEMS

CROSS-REFERENCE TO RELATED APPLICATIONS

This application is a continuation-in-part of U.S. Ser. No. 08/851,836 (U.S. Pat. No. 5,829,981), filed May 5, 1997.

FIELD OF THE INVENTION

The invention relates to the field of anatomical dental implant systems. More particularly, the invention relates to the field of impression copings for implant restorations.

BACKGROUND OF THE INVENTION

Dental restorative systems seek to provide cosmetic and functional replacements for missing teeth. Typically, methods for tooth replacement involve placement of an anchor, called a dental fixture, in the patient's jaw. The dental fixture is inserted into a hole drilled into the jaw. It provides a receptacle for the replacement tooth. Prior to replacement, however, an impression of the local dentition must be taken. The impression should preserve features of the dentition, including the position and alignment of the site for tooth replacement. An integral feature of this process is the use of an impression coping device, which serves to orient and preserve the impression of the local dentition. This allows a technician to form a replacement tooth that matches the contour and orientation of the natural teeth. The impression coping device typically is placed into the bore of the dental fixture, described above. In dental restorative systems of the art, a screw or bolt is used to anchor the impression coping device in the dental fixture. Once the impression coping device is screwed into the dental fixture, an impression of the local dentition can be taken.

Proper orientation of a replacement tooth is important both cosmetically and functionally. The impression coping device aids in this process by providing a substrate for an impression of the area in which tooth replacement will occur. The impression is formed around the impression coping device in a patient's mouth. The impression coping device and the attached impression are then removed from the patient's mouth, and are used as a basis for construction and orientation of a replacement tooth by a dental technician.

Typically, a screw assembly is used to secure an impression coping device to an implanted dental fixture. A dental fixture, therefore, generally consists of a central bore with screw threads for receiving a screw. The exposed surface (i.e., the surface of the fixture protruding from bone) of an implanted dental fixture typically consists of a hexagonal or round interface for defining the orientation of attachment of a tooth analog. An impression coping device is attached to the dental fixture by a screw that threads through the coping and into a central bore of the fixture. The screw mates with threads in the fixture in order to secure the impression coping. An impression of the dentition surrounding the tooth to be replaced is then taken. The impression then is removed from the mouth and used to fabricate a tooth analog, as indicated above.

In order to obtain a proper fit of the tooth analog, it is desirable to maintain rotational alignment between the implanted fixture and the patient's natural dentition. This requires that the impression coping device engage the implanted fixture in a non-rotational manner. Screw mechanisms used to secure impression copings tend to interfere with the rotational alignment of the impression.

Difficulties in handling and properly installing screws or bolts to secure coping devices have lead to improvements, such as an interlocking coping device comprising a screw that is non-removably inserted through the central bore, thus allowing insertion of the coping device and the screw in one step.

There remains, however, a need in the art for impression coping devices that are quicker and easier to use, and that resist rotational and other influences that cause misalignment of new tooth implants.

SUMMARY OF THE INVENTION

The present invention provides single-piece impression coping devices which allow easy visual inspection to determine whether the coping device has been properly positioned on a dental fixture. A coping device of the invention comprises the use of spaced-apart mating fingers which allow visual inspection to determine whether the coping is fully seated or engaged on the fixture in a proper spatial orientation. This allows quicker and easier tooth replacement, while maintaining the proper alignment of the replacement tooth with respect to the local dentition.

An impression coping device of the invention attaches to an implanted dental fixture by a radial friction fit between the coping device and a corresponding mating surface of the dental fixture. In a highly-preferred embodiment, the impression coping device forms a snap-fit connection with the dental fixture. In another embodiment, the impression coping device is seated or engaged on a dental fixture and is secured thereto with a fastener (e.g., a screw). Generally, a snap-fit connection differs from a friction-fit connection in that a snap-fit implies that a lip or other clasping mechanism exists to secure the fit between the impression coping device and the dental fixture. Both friction-fit and snap-fit mechanisms form a releasable coupling between the impression coping device and the dental fixture.

In one preferred embodiment of the invention, an impression coping device comprises a head. The head comprises a castellated end for releasably mating with a corresponding end of a dental fixture, the castellated end comprising axially-extending, radially-resilient fingers spaced apart sufficiently for viewing the fixture upon mating of the coping with the fixture, and a second end for attachment of an impression molding material. The mating portion of the head of the impression coping device forms a radial friction fit with its corresponding mating portion on the dental fixture. This causes releasable attachment of the impression coping device to the dental fixture. An impression of the local dentition can then be made. Once the impression is made, the impression coping device, along with impression molding material anchored to the second end of the head, is removed from the patient's mouth. Removal is accomplished by disengaging the radial friction fit between the coping device and the dental fixture.

Figure 4:
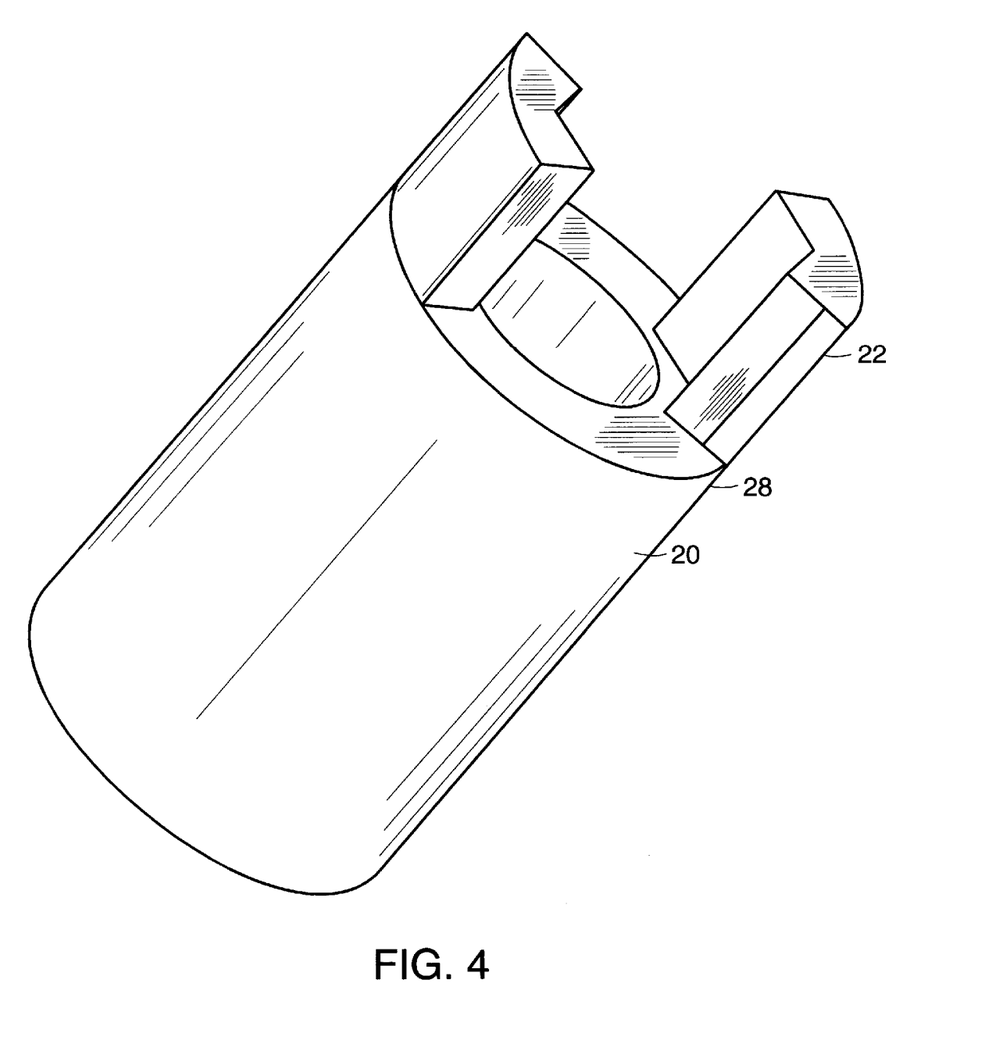
FIG. 4 is a stylized side view of an impression coping device of the invention.
Figure 5:
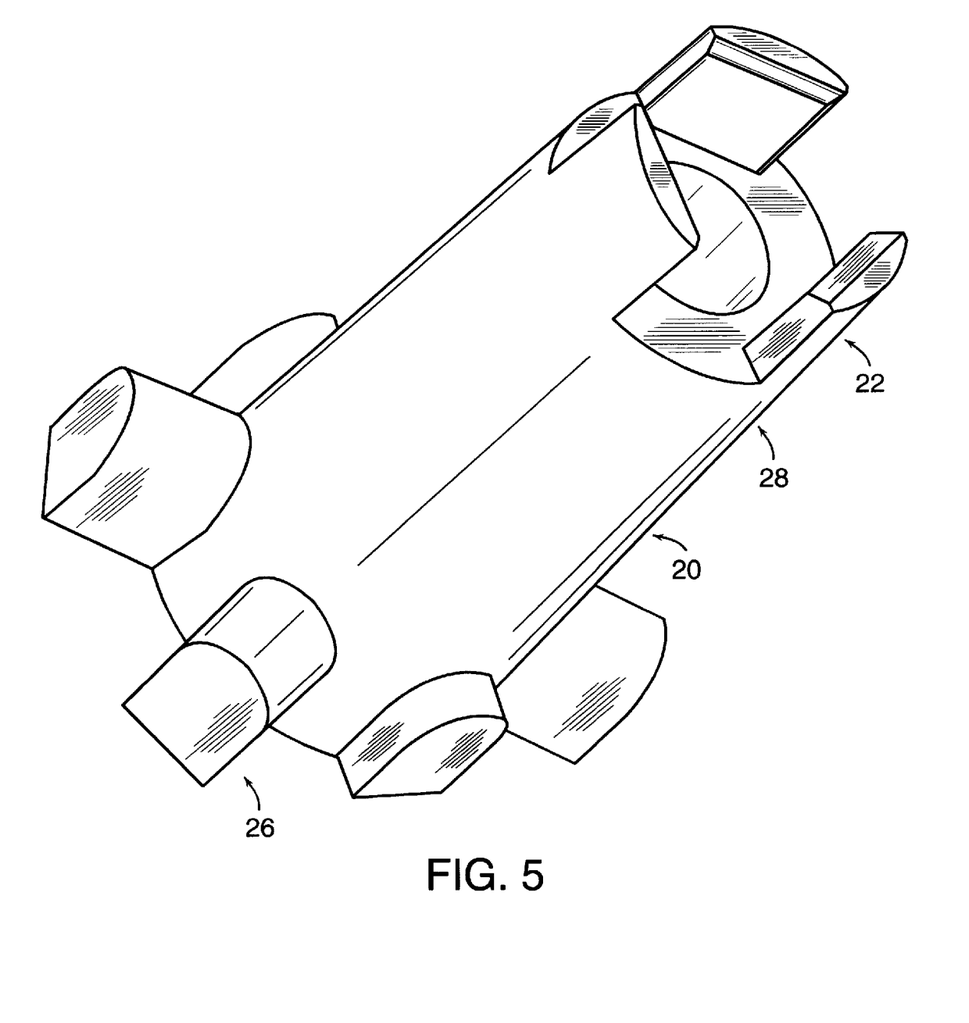
FIG. 5 is a side view of an impression coping device of the invention.

In a preferred embodiment, an impression coping device of the invention comprises a head having a castellated end for mating with a dental implant fixture, the castellated end comprising axially-extending, radially-resilient fingers spaced apart sufficiently for viewing the fixture upon mating of the coping with the fixture, and a second end to support an impression molding material. The castellated end may be any shape that is compatible with the interfacing surface of the fixture. Accordingly, the castellated end may be hexagonal, round, or any other shape that allows a mating interface to occur between the coping device and the fixture. In a preferred embodiment, shown in FIGS. 4 and 5 the castellated end comprises a plurality of axially extending, radially resilient fingers which expand to form a radial friction fit with a mating surface of a dental fixture. The fingers preferably are spaced apart so that when the impression coping device is mated to the fixture, one can visually inspect the fixture through the spaces between the fingers. Using spaced-apart fingers (e.g., as shown in FIGS. 4 and 5) assures that the dentist or technician can seat the impression coping on the fixture in its most advantageous spatial relationship with the fixture and the surrounding dentition. Thus, if the mating surface of the dental fixture comprises a male hexagonal interface, the inner surface of the fingers of the castellated end preferably comprise a female hexagonal interface. Also, in a preferred embodiment (e.g., as shown in FIG. 5) there are three fingers on the castellated end that are spaced apart so that, when the impression coping device is mated to the fixture, one can visually inspect the fixture through the spaces between the fingers. The coping can be secured to the fixture by a fastener, such as a screw which threads into the fixture.

Also in a preferred embodiment, the second end of the head of a device of the invention comprises at least one radially arranged flange protruding therefrom. Preferably, the second end comprises a plurality of radially arranged flanges. The flanges provide a substrate to anchor an impression molding material, which allows one to take an impression of the dentition in the vicinity of the replacement site(s).

An impression coping device of the invention preferably is constructed from a material such as, for example, polycarbonate or other resilient, moldable plastics or polymers. Also in a preferred embodiment, the head of a coping device of the invention is solid and has an outer surface that is substantially cylindrical in shape. A preferred inner diameter of the head is between about 3.00 mm and about 4.50 mm, and a preferred length of the head is between about 8.00 mm and about 9.00 mm. The overall length of device is preferably from about 13.00 mm to about 16.50 mm in length. The foregoing dimensions are based upon the dimensions of commonly-available dental fixtures. The skilled person recognizes that the dimensions of the impression coping device may be changed to accommodate a wide range of dental fixtures.

The invention will be understood further upon consideration of the following drawings, description and claims.

DETAILED DESCRIPTION OF THE INVENTION

The invention relates to an improved impression coping device for establishing the relative position of a dental implant. According to the invention, the coping device has spaced-apart castellated fingers at the point of attachment to a dental fixture. The spaced-apart fingers allow visual inspection of the attached coping device.

A device of the invention releasably attaches to a dental fixture by a friction-fit mating, a snap-fit mating, a threaded mating, or other mating means. A fastener (e.g., a screw) can be used for seating the coping device properly. As a result of the friction-fit mating between the impression coping device and the dental implant, the device may be inserted and removed without disturbing its rotational alignment with respect to the existing dentition. This makes it quicker and easier for a practitioner to make an impression of the local dentition that is useful for construction of a replacement tooth that has the same geometric architecture as the surrounding area into which the replacement tooth is placed. Thus, it is clear that an impression coping device of the invention may take many forms, depending, inter alia, on the dental fixture with which it mates, the location into which a replacement tooth is placed, the surface area necessary or desirable for anchoring an impression, and other factors known to the skilled person. Described below is a preferred embodiment of the invention for use with standard dental fixtures.

Figure 1A:
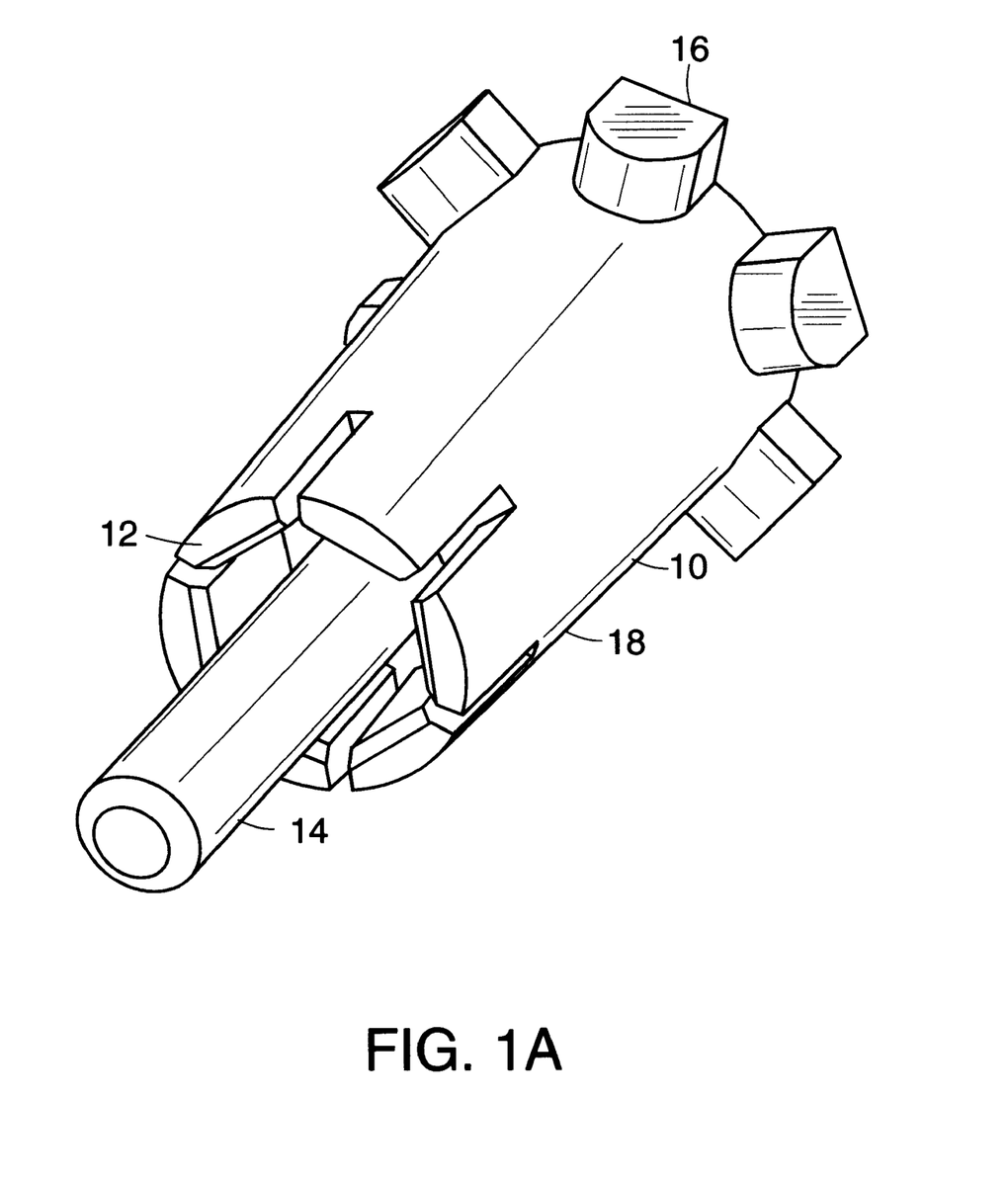
FIG. 1A illustrates a bottom view of an impression coping device of the invention.
Figure 1B:
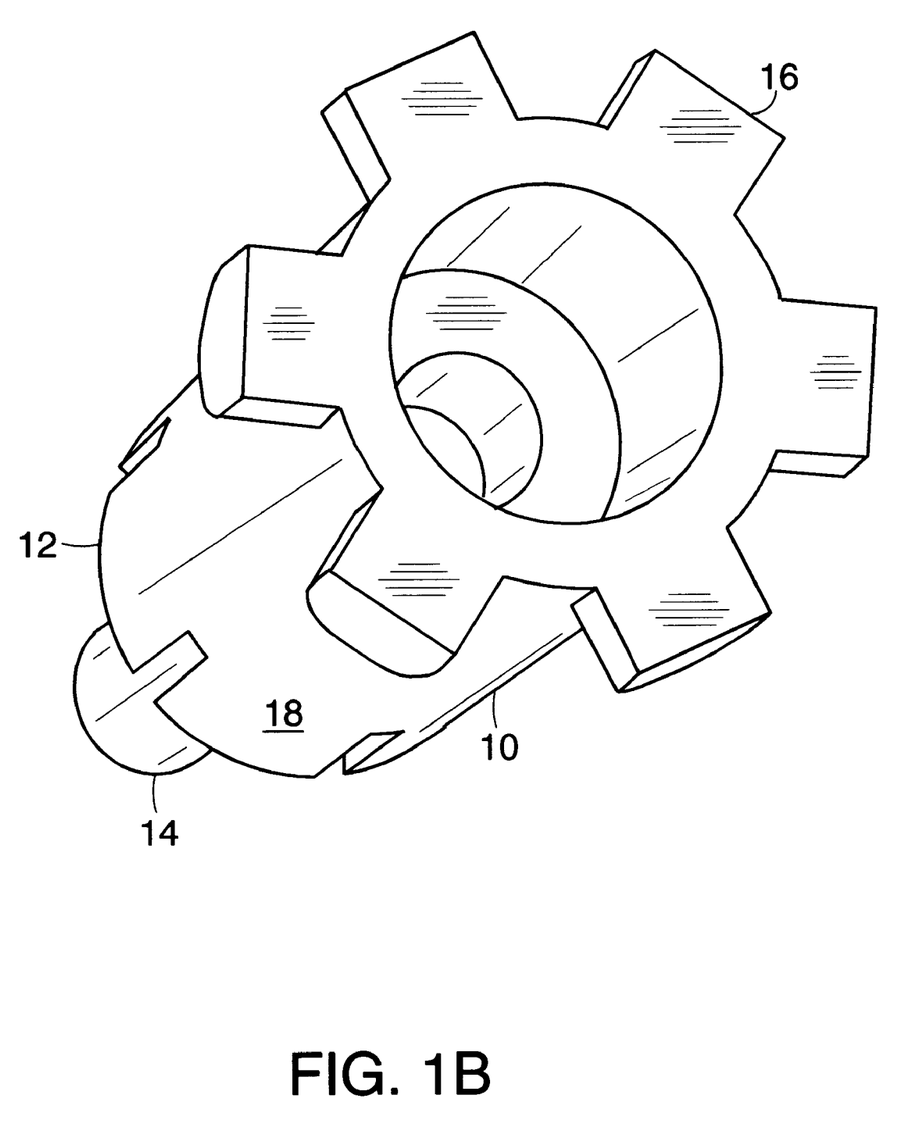
FIG. 1B illustrates a top view of an impression coping device of the invention.
Figure 2A:
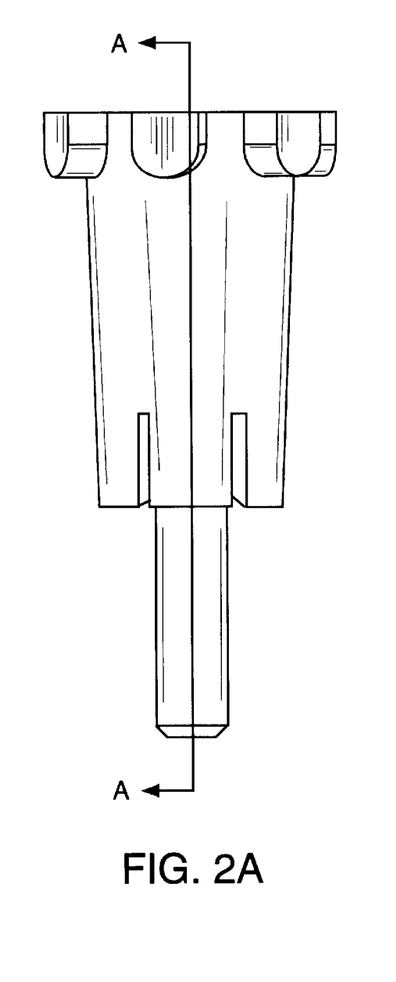
FIG. 2A is a side view of an impression coping device of the invention.
Figure 2B:
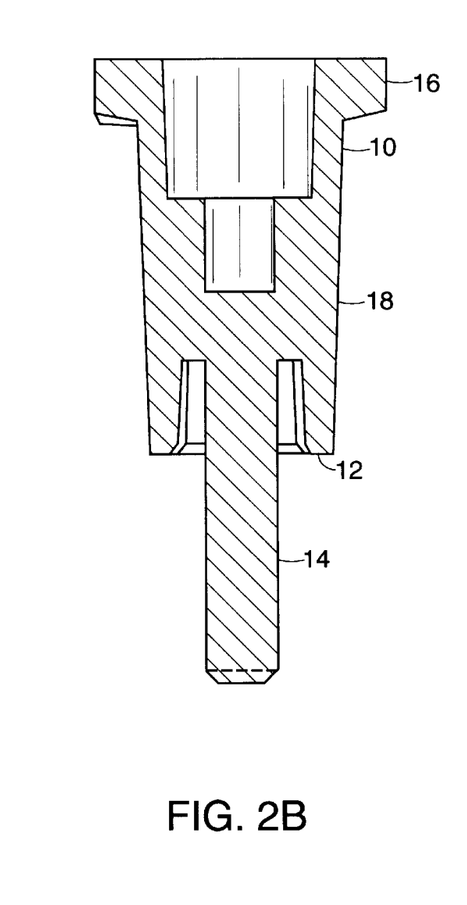
FIG. 2B is a cross-sectional view of the device shown in FIG. 2A.

A preferred device of the invention comprises a head having a first end that releasably attaches to a dental fixture. The first end preferably is castellated, as shown in FIGS. 1A and 1B. The castellated end comprises a plurality of axially extending, radially resilient fingers that deflect as they are friction fitted over a mating surface of a dental fixture. Further, the castellated end comprises an inner surface which corresponds to mating detail on the surface of a dental fixture. Expansion of the fingers causes the castellated end to radially friction fit onto the reciprocal mating surface of the fixture.

The radial friction fit between corresponding mating surfaces of the impression coping device and the dental fixture allows releasable attachment of the device to the dental fixture with or without the use of screws. Thus, the orientation and alignment of an impression of the local dentition are preserved.

Figure 3:
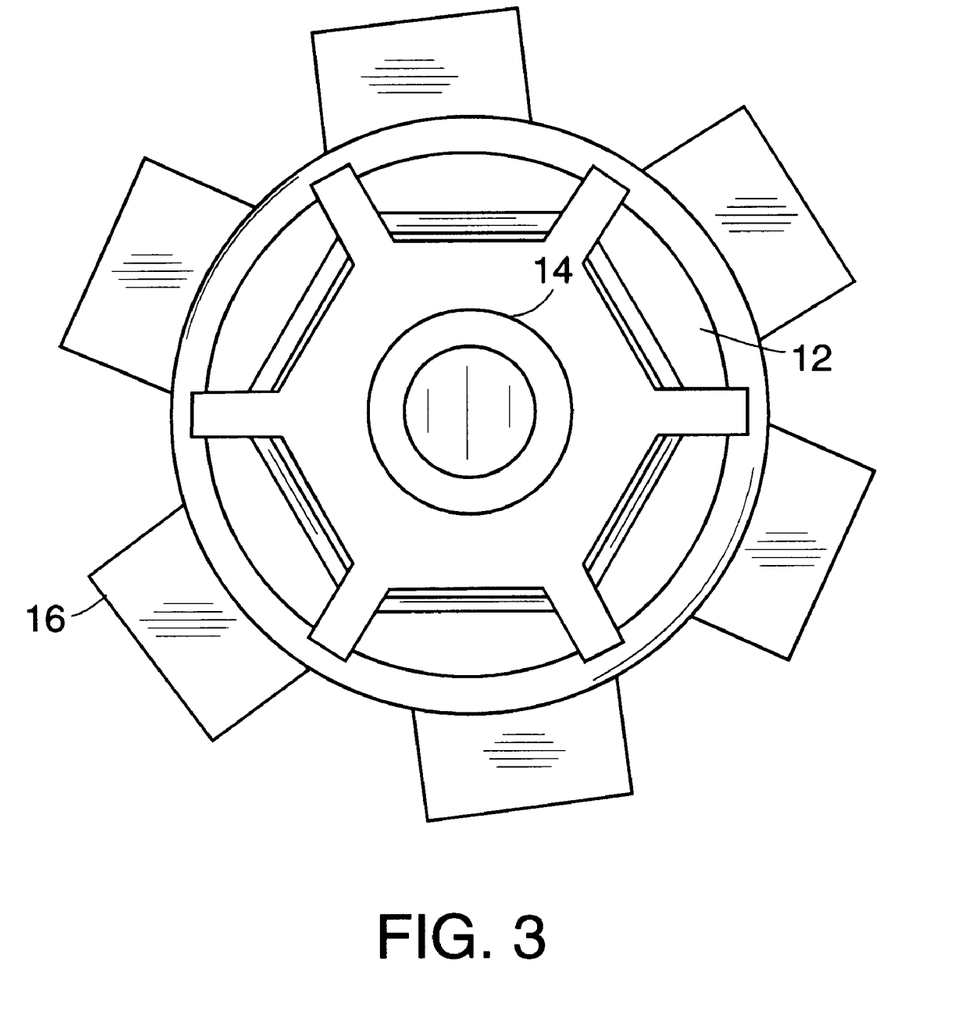
FIG. 3 is a bottom view of an impression coping device of the invention.

A preferred impression coping device of the invention is shown in FIG. 1A. It has a first end comprising a head 10 that is substantially frusto-conical or cylindrical in shape. The head has a castellated end 18, which has a hexagonal inner surface for mating with a corresponding surface of a dental fixture (not shown). The castellated end of the head comprises axially-extending, radially-resilient fingers 12, which form a flexible hexagonal inner surface for providing a radial friction fit with a corresponding dental fixture mating surface. FIG. 3 shows a hexagonal mating detail of a device of the invention. Like reference numerals in FIGS. 1B and 3 refer to like elements in FIG. 1A. The hexagonal mating detail makes reciprocal contact with a corresponding mating detail on a dental fixture in order to hold the impression coping device in place.

A particularly-preferred impression coping device of the invention is shown in FIG. 5. The device has a first end comprising a head 20 that is substantially frusto-conical or cylindrical in shape. The head has a castellated end 28, which has an inner surface that is complementary to a hexagon for mating with a corresponding surface of a dental fixture (not shown). The castellated end of the head preferably comprises three spaced-apart axially-extending, radially resilient fingers 22, which form a flexible inner surface that is complementary to a hexagon for providing a radial friction fit with a corresponding dental fixture mating surface. FIG. 4 shows an alternative embodiment of the impression coping device with two axially-extending, radially resilient fingers. Like reference numerals in FIGS. 4 and 5 refer to like elements. The spacing between fingers allows visual inspection of the coping device as attached to the fixture. The ability to visually inspect the attached device/fixture ensures that a proper mating has been achieved between the coping and the fixture (i.e., that the mating has retained proper geometry for taking an accurate impression). The spacing between fingers can be any distance that allows for visual inspection of the coping device as attached to the fixture. A preferred spacing of the fingers is between 0.5 mm and 3 mm. A particularly preferred spacing is between 1 mm and 2 mm.

A second end of the head comprises one or more radially arranged flanges 16. These are arranged to provide an anchor for impression molding material applied to the dentition in the vicinity of the replacement site. The flanges provide surface area for attachment of the molding material, thereby facilitating its removal from the mouth upon curing.

In a preferred embodiment, an impression coping device of the invention is constructed from a biologically compatible material. Preferred biologically compatible materials include, but are not limited to, polycarbonate, high-impact polystyrene, and polyetherimide.

An impression coping device of the invention is made by well-known processes. Such processes include, for example, injection-molding or stereolithography. The precise method for manufacturing an impression coping device of the invention is immaterial to practice of the invention, as long as a device results from such process that forms a releasable friction fit with a dental fixture, as described above.

An impression coping device of the invention is used as an aid in performing a single or multiple tooth restoration. Generally, a study cast of a patient's existing teeth is first made. Then, a dental fixture, such as that manufactured by Life Core, is implanted in a bore hole made in a patient's jaw at the site of desired tooth replacement. The implant site is surgically prepared by drilling into the jawbone after the gingival tissue surrounding the point of insertion of the implant has been retracted.

A preferred dental fixture comprises a male hexagonal interface at its exposed end and is therefore compatible with an impression coping device of the invention having a female hexagonal interface on the castellated end of the head. As described above, the dental fixture also contains a hollow bore, which is open from the exposed end of the fixture and extends into the fixture. The hollow portion of the implant fixture may or may not have inner screw threads.

A coping device of the invention is attached to the implanted dental fixture using a radial friction fit that is formed between the castellated end of the impression coping device and the corresponding hexagonal mating end of the dental fixture. The fingers of the castellated end expand as the device is forced over the male hexagonal interface of the fixture. The radial friction fit between the two hexagonal interfaces prevents the coping device from rotating on the fixture. Similarly, a snap-fit connection may be used in which the mating end of the impression coping device comprises a lip that fits over the mating surface of the dental fixture, forming a removable or releasable communication between the two.

In a particularly preferred embodiment, the coping device of the invention is attached by a radial friction fit formed between the castellated end with three axially-extending, radially resilient fingers and the corresponding hexagonal mating end of the dental fixture. The three fingers provide for an easy visual determination of whether the coping device is properly engaged or seated with the dental fixture. The fingers of the castellated end expand as the device is forced over the male hexagonal interface of the fixture. The radial friction fit prevents the coping device from rotating on the fixture. Similarly, a snap-fit connection may be used in which the mating end of the impression coping device comprises a lip that fits over the mating surface of the dental fixture, forming a removable or releasable connection between the two. Such a device is not clamped to a fixture, but is seated on the flats or "points" on the mating hex on the fixture, thereby providing a mating fit with resistance to rotation, but not requiring a clamping force.

The spaced-apart fingers provide for easy visual determination of whether the coping device is properly engaged or seated with the dental fixture. The spacing between fingers can be any distance that allows for visual inspection of the coping device as attached to the fixture. A preferred spacing of the fingers is between 0.5 mm and 3 mm. A particularly preferred spacing is between 1 mm and 2 mm. Alternatively, a castellated end with two axially-extending, radially resilient fingers, also is useful for visual determination of proper engagement or seating in either a friction-fit or snap-fit configuration. A fastener (e.g., a screw) can be used for seating the coping device properly.

After the impression coping device is attached to the dental fixture, an impression of the local dentition is made. An elastomeric impression material, such as, for example, polyether siloxane or polyvinyl siloxane, is pressed onto the coping device and surrounding teeth. The impression preferably is made without contacting the gum tissue. The impression is allowed to harden for approximately one minute before removal. Once the impression is formed, the impression coping device, and attached impression material, are removed by pulling the coping away from the dental implant fixture. The coping and the impression are removed simultaneously. After the impression is made, the gingival tissue is replaced over the bone and around the implanted dental fixture to promote healing. Healing generally occurs within about 4 to about 9 months.

The impression coping device containing the attached impression material is attached to an analog fixture, which is then cast in a study cast previously made of the patient's mouth. The space surrounding the analog fixture is then filled and allowed to cure so that the analog fixture becomes part of the study cast. The rotational and positional alignment of the dental fixture is thus preserved with respect to the patient's natural dentition.

A pre-fabricated abutment, over which a crown is placed, is then constructed. A series of measurements are taken in order to guide the fabrication of an abutment and crown that closely approximate the tooth being replaced. Measurements are taken from all directions with respect to the angles of adjacent teeth and/or face construction. Measurements required to fabricate and position abutments for teeth are provided, for example, in Wheeler, *Dental Anatomy, Physiology and Occlusion* (5th ed. 1974), incorporated by reference herein. Measurements may be taken by several means including, but not limited to, a stent, a mold of the teeth, an optical device, or other measuring instrument.

Using these measurements, an abutment is fabricated for insertion into the implanted dental fixture. Measurements may be made using a computerized abutment model, as disclosed in co-owned, co-pending U.S. patent application Ser. No. 08/372,323, incorporated by reference herein. The computer model is based on general abutment parameters for the particular tooth or teeth being replaced. Based upon the computer model, a wax model of the abutment is created on, for example, a Sanders Prototype, Inc. Model Maker 6 Pro® rapid prototyping machine. A crown that approximates the size and color of the patient's natural teeth is fabricated to fit over the abutment. A dental technician sculpts the crown with reference to the previously-prepared analog fixture and abutment. The crown is sculpted from, for example, wax or ceramic. The skilled artisan is aware that numerous methods may be used to fabricate an abutment and crown from an impression molding.

After the site of the implanted dental fixture in the patient's jawbone is healed, the abutment is screwed into place in the dental fixture. The crown is attached to the abutment with an adhesive and/or a lateral set screw.

An implant restoration is, therefore, performed without the necessity of screwing an impression coping into a dental fixture implanted in a patient's jaw. The impression coping device of the invention makes it quicker and easier for a practitioner to prepare a crown and abutment, while preserving the exact rotational and positional alignment of the patient's natural dentition.

Additional aspects and advantages of the invention are apparent upon consideration of the foregoing. Accordingly, the scope of the invention is limited only by the scope of the appended claims.

What is claimed is:

1. An impression coping device, comprising:
 a head comprising a castellated end for releasable mating with a dental fixture, wherein said castellated end comprises axially-extending, radially-resilient fingers spaced apart sufficiently for viewing said fixture upon mating with said fixture, and a second end having a plurality of substantially coplanar, radially-arranged flanges for attachment of an impression material.

2. The device of claim 1, wherein said releasable mating is a friction-fit mating.

3. The device of claim 1, wherein said releasable mating is a snap-fit mating.

4. The device of claim 1, wherein an inner surface of said fingers are complementary to an interface of said dental implant fixture.

5. The device of claim 4, wherein said inner surface comprises a female interface to a hexagonal shape.

6. The device of claim 1, wherein said device is constructed from a material selected from the group consisting of polycarbonate, high-impact polystyrene and polyetherimide.

7. The device of claim 1, wherein said head has an inner diameter of between about 3.00 mm and about 4.50 mm.

8. The device of claim 1, wherein said head has a length of between about 8.00 mm and about 9.00 mm.

9. The device of claim 1, wherein said device has a length of between about 13.00 mm and about 16.50 mm.

10. An impression coping device, comprising:
 a head comprising a castellated end for releasable mating with a dental fixture, wherein said castellated end comprises three axially-extending, radially-resilient fingers spaced apart sufficiently for viewing said fixture upon mating with said fixture, and a second end having a plurality of substantially coplanar, radially-arranged flanges for attachment of an impression material.

* * * * *